United States Patent
Keilman et al.

[11] Patent Number: 5,873,853
[45] Date of Patent: Feb. 23, 1999

[54] PORTABLE PUMP APPARATUS FOR CONTINUOUS AMBULATORY PERITONEAL DIALYSIS AND A METHOD FOR PROVIDING SAME

[75] Inventors: Michael R. Keilman, Johnsburg; Kelly B. Smith, Gurnee, both of Ill.

[73] Assignee: Baxter International Inc., Deerfield, Ill.

[21] Appl. No.: 448,057

[22] Filed: May 23, 1995

[51] Int. Cl.⁶ .................................................. A61M 31/00
[52] U.S. Cl. ............................................................ 604/67
[58] Field of Search ........................ 604/28, 64, 65–67, 604/30–34, 49, 50, 53, 151

[56] References Cited

U.S. PATENT DOCUMENTS

| | | |
|---|---|---|
| 3,989,913 | 11/1976 | Lundquist et al. . |
| 4,063,554 | 12/1977 | Willock et al. . |
| 4,102,612 | 7/1978 | Ritter ..................................... 427/477 |
| 4,244,787 | 1/1981 | Klein et al. . |
| 4,316,466 | 2/1982 | Babb ........................................ 604/66 |
| 4,396,382 | 8/1983 | Goldhaber . |
| 4,398,908 | 8/1983 | Siposs . |
| 4,631,008 | 12/1986 | Stenner . |
| 4,710,165 | 12/1987 | McNeil et al. . |
| 4,820,265 | 4/1989 | DeSatnick et al. ....................... 604/65 |
| 5,114,580 | 5/1992 | Ahmad et al. .......................... 210/656 |
| 5,141,493 | 8/1992 | Jacobsen et al. ......................... 604/28 |
| 5,170,817 | 12/1992 | Sunderland . |
| 5,205,819 | 4/1993 | Ross et al. . |
| 5,232,439 | 8/1993 | Campbell et al. . |
| 5,244,463 | 9/1993 | Cordner, Jr. et al. . |
| 5,246,347 | 9/1993 | Davis . |
| 5,350,357 | 9/1994 | Kamen et al. . |
| 5,395,320 | 3/1995 | Padda et al. .............................. 604/65 |
| 5,423,746 | 6/1995 | Burkett et al. ............................ 604/65 |
| 5,437,635 | 8/1995 | Fields et al. .............................. 604/65 |
| 5,630,799 | 5/1997 | Beiser et al. .............................. 604/66 |

FOREIGN PATENT DOCUMENTS

| | | |
|---|---|---|
| 0243547 | 11/1987 | European Pat. Off. . |
| 0402505 | 6/1989 | European Pat. Off. . |

*Primary Examiner*—Manuel Mendez
*Attorney, Agent, or Firm*—Charles R. Mattenson; Thomas S. Borecki; Robert M. Barrett

[57] ABSTRACT

A portable pump apparatus for use in CAPD is provided as well as a method for providing CAPD to a patient. The portable pump apparatus for CAPD has a housing containing a pump, and a power supply, preferably a rechargeable battery, connected to the housing and electrically connected to drive the pump. A control knob on the housing is constructed and arranged to adjust the speed of the pump. A cover is mounted to the housing to enclose the pump. The cover has an inlet port and an outlet port to securely hold a tube thereunder. The portable pump apparatus for CAPD further has a display for providing drainage information and a clip so that the apparatus can be worn by a patient.

10 Claims, 3 Drawing Sheets

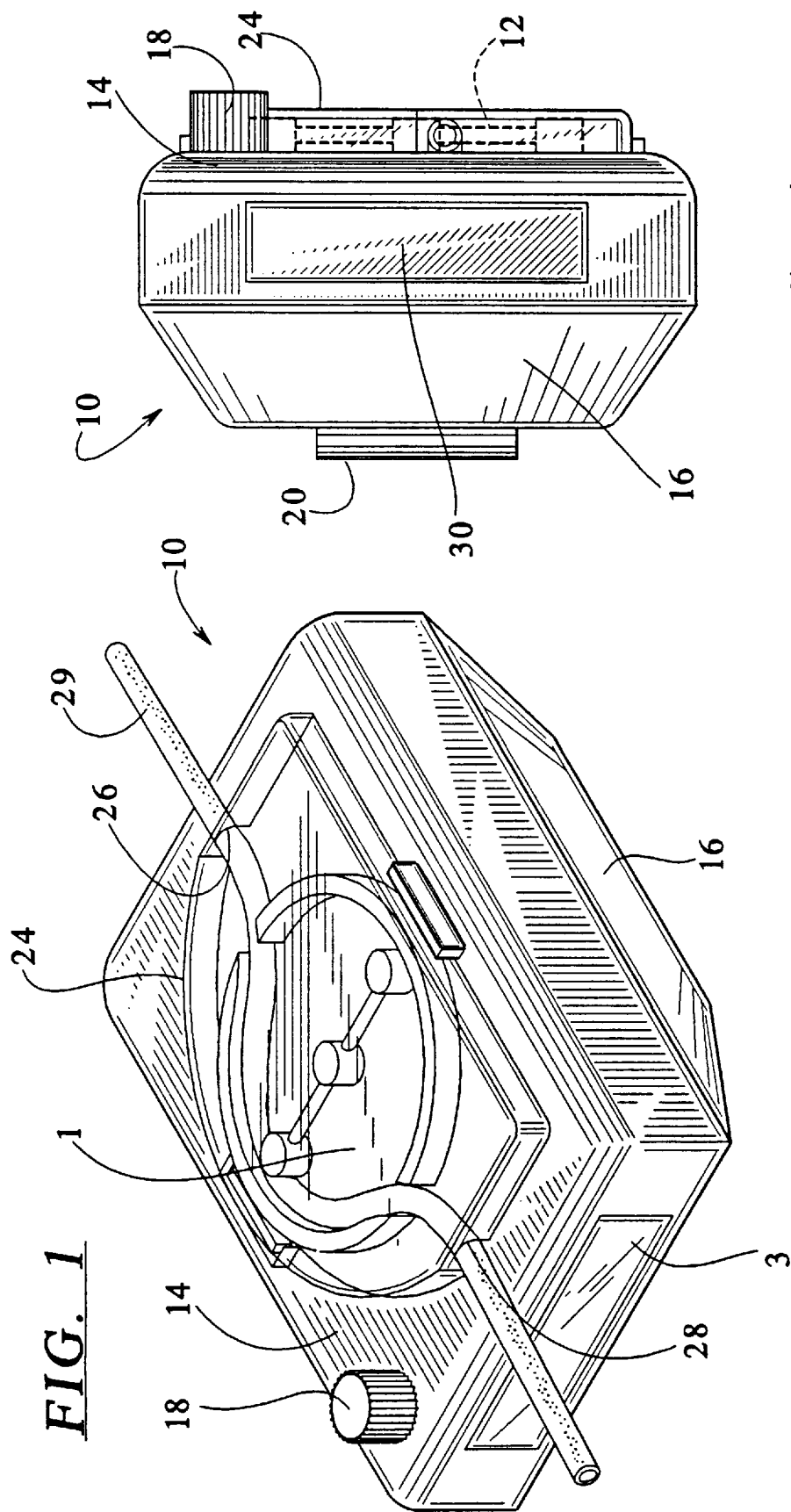

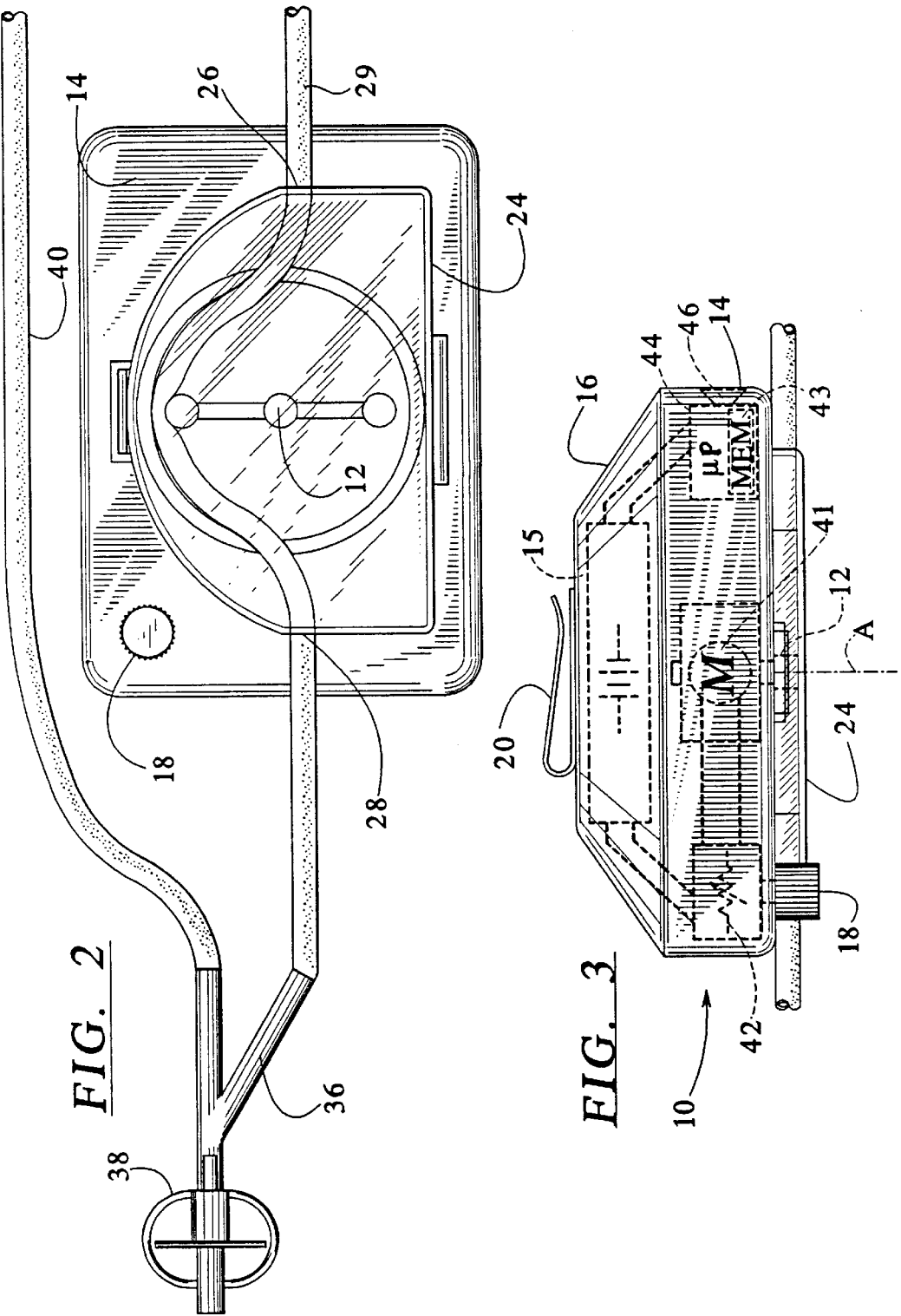

PORTABLE PUMP APPARATUS FOR CONTINUOUS AMBULATORY PERITONEAL DIALYSIS AND A METHOD FOR PROVIDING SAME

BACKGROUND OF THE INVENTION

The present invention relates generally to treatment of patients using continuous ambulatory peritoneal dialysis (CAPD). More specifically, the present invention relates to a portable pump apparatus for CAPD and a method for providing CAPD to a patient.

It is known to use dialysis to support a patient whose renal function has decreased to the point where the kidneys no longer sufficiently function. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, there are certain inherent disadvantages with hemodialysis.

To overcome the disadvantages associated with hemodialysis, peritoneal dialysis was developed. Peritoneal dialysis utilizes the patient's own peritoneum as a semi-permeable membrane. The peritoneum is a membranous lining of the abdominal body cavity that due to a large number of blood vessels and capillaries is capable of acting as a natural semi-permeable membrane.

In continuous ambulatory peritoneal dialysis, a dialysis solution is introduced into the peritoneal cavity utilizing a catheter. Solutes (e.g., urea, creatinine, etc.) diffuse from the blood into the dialysate due to the presence of a diffusion gradient. Similarly, the presence of an osmotic gradient between the peritoneal cavity and the blood causes fluid to be removed from the body into the dialysate which is then drained through the catheter. These processes allow the proper chemical and fluid balance to be returned to the body.

After a sufficient period of time, an exchange of solutes between the dialysate and the blood is achieved. Fluid removal is achieved by providing a suitable osmotic gradient from the blood to the dialysate to permit water out flow from the blood. This allows the proper acid-base, electrolyte and fluid balance to be returned to the blood, and the dialysis solution is simply drained from the body cavity through the catheter.

Peritoneal dialysis raises a number of issues including: the danger of peritonitis; a lower efficiency and therefore increased duration of dialysis hours compared to hemodialysis; and cost issues when automated equipment is utilized.

A number of variations on peritoneal dialysis have been explored. One such variation is reciprocating, recirculating, or semi-continuous peritoneal dialysis. In such systems, dialysis solution is infused into the peritoneal cavity and then, typically, on a continuous process basis a portion of the dialysis solution is sequentially drained, cleansed, and reinfused.

Currently, a CAPD patient drains the peritoneal cavity by means of gravity alone. This however is rather time consuming. For example, the drainage takes about fifteen minutes on the average, depending on the patient's body position. As such, CAPD is relatively inconvenient for the patient.

Certain attempts have been made to improve the process of draining fluid from a patient. For example, U.S. Pat. No. 4,710,165 to McNeil et al. discloses a wearable, variable rate suction and collection device for the withdrawal and collection of fluid from a patient. Also, U.S. Pat. No. 4,316,466 to Babb discloses a body fluid drainage device which may be mounted externally on the body of a patient and may be driven by a portable source of power. In addition, recycled effluent systems are currently used but are not portable.

Therefore, a need has arisen for a portable drainage pump apparatus to assist flow and to improve CAPD drainage times.

SUMMARY OF THE INVENTION

The present invention provides an improved CAPD apparatus and a method for providing CAPD to a patient. The apparatus for use in the method comprises a portable pump apparatus for reducing the time necessary for conducting CAPD.

To this end, a portable pump apparatus for providing CAPD to a patient is provided. The apparatus comprises: a housing; a pump located in the housing; a power supply electrically connected to the pump to energize the pump; and a cover mounted to the housing to enclose the pump, the cover having an inlet port and an outlet port constructed and arranged to securely hold a tube restricting motion of the tube outside of the cover.

In an embodiment, the portable pump apparatus for CAPD further comprises a control means constructed and arranged for adjusting the speed of the pump.

In an embodiment, the portable pump apparatus for CAPD further comprises a fastening means constructed and arranged on the housing for providing attachment to a patient.

In an embodiment, the power supply is a rechargeable battery.

In an embodiment, the pump is a reversible roller pump.

In an embodiment, the portable pump apparatus for CAPD further comprises means for displaying CAPD information located on the housing.

In an embodiment, the portable pump apparatus for CAPD further comprises means for processing operatively connected to the pump.

In an embodiment, the portable pump apparatus for CAPD further comprises a volume sensor connected to the means for processing.

In an embodiment, the portable pump apparatus for CAPD further comprises means for determining urea clearance data connected to the means for processing.

In an embodiment, the means for processing is a microprocessor.

In an embodiment, the portable pump apparatus for CAPD further comprises means for measuring CAPD data connected to the means for processing.

In an embodiment, the portable pump apparatus for CAPD further comprises means for storing CAPD data connected to the means for processing.

In an embodiment, the portable pump apparatus for CAPD further comprises an alarm means connected to the means for processing.

In another embodiment, a portable pump apparatus for conducting CAPD by pumping a fluid into a patient and an effluent out of a patient is provided. The apparatus comprises a power source; a length of tubing having a first end connectable to a container holding fluid and a second end connectable to a patient; means for pumping the fluid from the container into the patient and the effluent out of the patient into the container, the means for pumping connected to the power source.

In an embodiment, the portable pump apparatus for CAPD further comprises means for varying the speed of the means for pumping.

In an embodiment, the portable pump apparatus for CAPD further comprises means for storing the at least one CAPD parameter.

In an embodiment, the portable pump apparatus for CAPD further comprises means for processing the at least one CAPD parameter.

In an embodiment, the portable pump apparatus for CAPD further comprises means for removably attaching the means for pumping to a patient.

In an embodiment, the portable pump apparatus for CAPD further comprises a cover constructed and arranged on the means for pumping, the cover having at least one port capable of holding the length of tubing restricting movement of the tubing outside the cover.

In an embodiment, the cover is constructed of a transparent material.

In an embodiment, the portable pump apparatus for CAPD further comprises means for determining at least one CAPD parameter.

In an embodiment, the at least one CAPD parameter is volume of effluent displaced.

In another embodiment, a method for providing CAPD to a patient is provided. The method comprises the steps of: providing a portable pump apparatus for CAPD; connecting the portable pump apparatus to a source of dialysate; pumping the dialysate into the patient using the portable pump apparatus; and pumping effluent out of the patient using the portable pump apparatus.

In an embodiment, the method further comprises the step of monitoring urea clearance.

In an embodiment, the method further comprises the step of displaying urea clearance information on the portable pump apparatus.

In an embodiment, the method further comprises the step of monitoring volume of effluent displaced.

It is, therefore, an advantage of the present invention to provide an extremely small, portable pump apparatus and a method for use in CAPD that uses existing pump technology.

Another advantage of the present invention is to provide a portable pump apparatus and method that monitors and stores parameters including effluent volume display and urea clearance for monitoring adequacy over time.

Moreover, an advantage of the present invention is to provide a pump apparatus that is portable and small enough to be worn on, for example, a belt of a patient.

Yet another advantage of the present invention is to provide a pump apparatus that includes a rechargeable battery.

A further advantage of the present invention is to provide a portable pump apparatus and method having a reduced drain time for more solution dwell time providing more adequacy for the patient.

Another advantage of the present invention is to provide a small, portable pump apparatus and method for CAPD to hasten the fill process of the CAPD exchange.

Still another advantage of the present invention is to provide a portable pump apparatus and method having a number of safety features including, for example, an automatic shut-off and an alarm that sounds when the peritoneum is nearly empty or when occluded tubing is sensed, for example.

Another advantage of the present invention is to provide a pump speed control in the form of a user knob that can be adjusted by the patient to a comfortable rate during the use of the present invention.

Also, a further advantage of the present invention is to provide a protective cover over the pump securely holding the tubing to avoid tugging the catheter during pumping.

Moreover, an advantage of the present invention is to provide a portable pump device for use in CAPD that provides greater patient comfort and convenience by means of a small, lightweight, ergonomically-designed apparatus.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of an embodiment of a portable pump apparatus for CAPD of the present invention.

FIG. 2 illustrates a front view of an embodiment of the portable pump apparatus for CAPD of the present invention.

FIG. 3 illustrates an end elevational view of an embodiment of the portable pump apparatus for CAPD of the present invention.

FIG. 4 illustrates a plan view of an embodiment of the portable pump apparatus for CAPD of the present invention.

DETAILED DESCRIPTION OP THE PRESENTLY PREFERRED EMBODIMENTS

Figure 5:
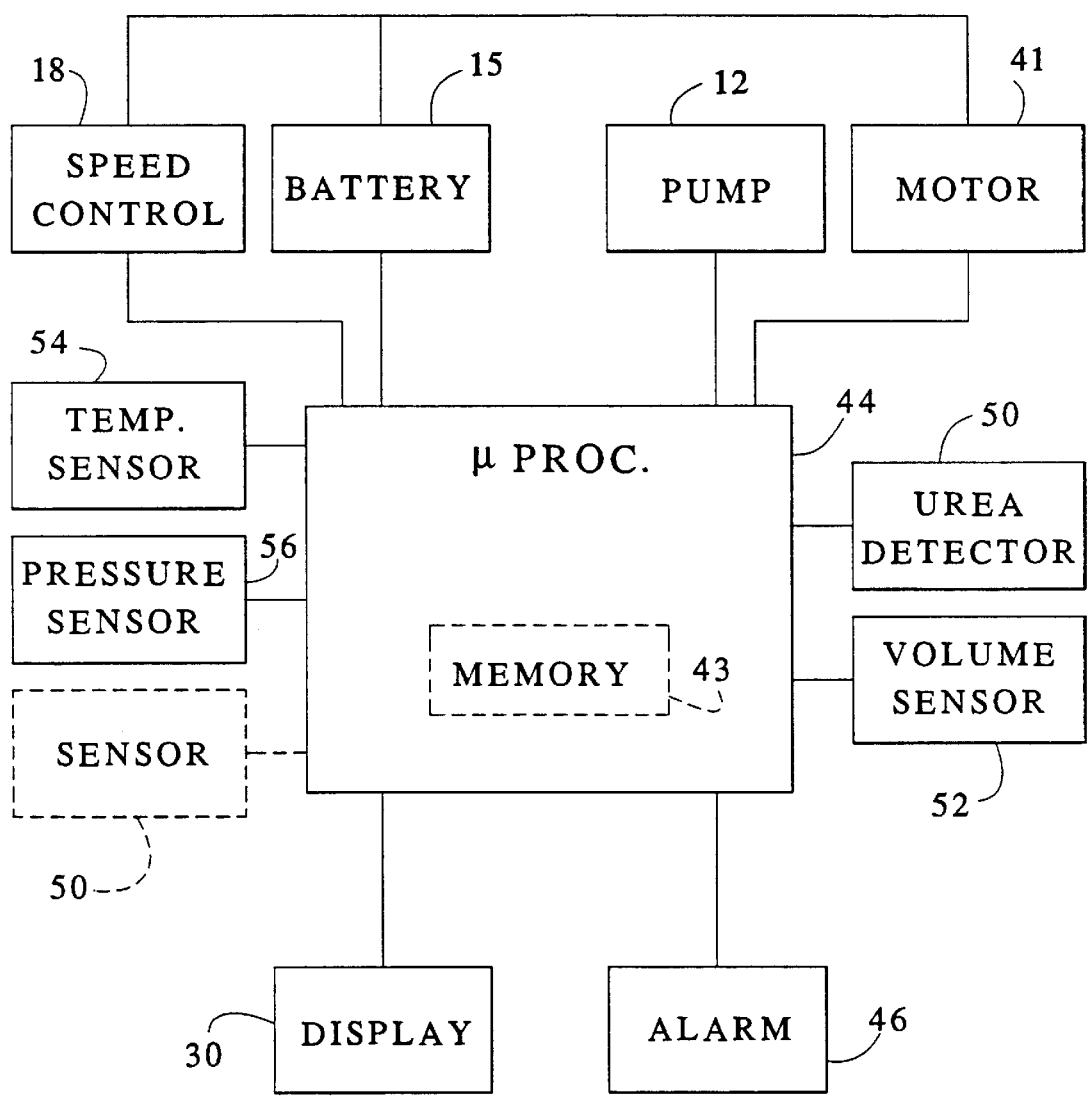
FIG. 5 illustrates a functional block diagram of an embodiment of the portable pump apparatus for CAPD of the present invention.

The present invention provides a portable pump apparatus for providing CAPD to a patient and method for providing CAPD to a patient. Specifically, the present invention provides a wearable apparatus for CAPD having a single pump driven by a rechargeable battery.

Referring to FIG. 1, a portable drainage pump apparatus for CAPD is generally illustrated at 10. The pump apparatus 10 has a pump 12 located in a housing 14 of the pump apparatus 10. The portable pump apparatus 10 for CAPD is preferably battery-powered. To this end, a rechargeable battery 15 (see FIG. 3) is electrically connected to the pump 12 in the housing 14 of the pump apparatus 10. The rechargeable battery 15 is located in a section 16 of the housing 14 to decrease the size of the pump apparatus 10.

In addition, the speed of the pump 12 may be adjusted by the patient via a speed control knob 18 conveniently located on the housing 14. The peritoneal dialysis patient can simply adjust the speed of the pump 12 by using the speed control knob 18. The pumping speed can thereby be adjusted to a comfortable level.

To make the present invention more convenient to use and to wear, a belt clip 20 is also provided. The belt clip 20 is preferably connected to the housing 14 of the pump apparatus 10. The belt clip 20 is constructed and arranged to enable the pump apparatus 10 to be conveniently clipped on a belt or a waistband of an individual using the pump apparatus 10, i.e. a CAPD patient. Of course, other means for securing the pump apparatus 10 to an individual may be implemented by those skilled in the art.

Also shown in FIG. 1 is a protective cover 24 arranged to enclose the pump 12. The cover 24 is preferably made of a clear or transparent material so that the pump 12 can be observed in operation. The protective cover 24 has an inlet port 26 and an outlet port 28 formed therein through which a drain tube 29 extends. The drain tube 29 is, therefore, in communication with the pump 12 when positioned as illustrated in FIGS. 1 and 2. Also illustrated in FIG. 1 is a display 30, preferably digital, provided for the convenience of the user. The display 30 is provided for monitoring certain parameters for example.

FIG. 2 illustrates an embodiment of the portable drainage pump apparatus 10 for CAPD of the present invention having the drain tube 29. The drain tube 29 is fed through the inlet port 26 of the cover 24. The drain tube 29 is in communication with the pump 12 and exits the protective cover 24 at the outlet port 28. Also shown is a Y-connector 36 and a fitment 38. The Y-connector 36 is further connected to a fill tube 40.

In the embodiment of the pump apparatus 10 illustrated in FIG. 2, a bag of dialysate (not shown) is provided. The dialysate can be any peritoneal dialysis solution desired. The dialysate is connected in fluid communication by the fill tube 40 to the Y-connector 36.

Referring still to FIG. 2, as illustrated, the present invention provides the pump apparatus 10 for CAPD including the single pump 12 that is used to pulse fluid into and out of the peritoneal cavity of the patient. Unlike some of the prior art systems that require multiple pumps and circuits resulting in complicated systems that are difficult to set up and that are expensive, the present invention provides only a single pump.

In an embodiment, fluid (dialysate) is pumped into and out of the patient by use of the pump 12. In a preferred embodiment, as illustrated, the pump 12 is a reversible roller type pump. The pump 12 is arranged to act on the drain tube 29. The pump 12 operates in the known manner of a reversible roller pump. The pump 12 can cause fluid to move in either direction through either the drain tube 29 or the fill tube 40. For example, the fill tube 40 may be arranged and held under the cover 24 so that dialysate or other fluid may be pumped into the patient by using the pump 12.

Pursuant to the present invention, by use of the pump 12, the fluid (dialysate) can be transported via small stroke volumes. The roller pump 12 rotates on an axis A (see FIG. 3) driven by a motor 41. Power to the motor 41 is supplied by the battery 15, preferably a rechargeable battery. As stated above, the speed of the motor 41 can be controlled by the knob 18 connected to a variable resistor 42 for example. In addition, the fill tube 40 extends to the patient and terminates at a catheter (not shown) that is in fluid communication with the peritoneal cavity of the patient.

Also, as stated above, the speed control knob 18 allows the patient to adjust the pumping to a comfortable rate. The control knob 18 is connected to the variable resistor 42 which is in turn connected to the motor 41 as shown in FIG. 3. Further, the protective cover 24 also secures the drain tube 29 to prevent the pumping motion from tugging on the catheter that is located in the patient. For example, when the pump 12 is rotating in communication with the drain tube 29 to aid in the drainage of fluid from the peritoneum, the drain tube 29 can be moved or tugged by the pulsing rotation of the pump 12, which in turn causes the drain tube 29 to move slightly. To alleviate this tugging, the cover 24 has the inlet port 26 and the outlet port 28 which are appropriately sized, as well as constructed and arranged to securely hold the drain tube 29. In this manner, only that portion of the drain tube 29 located inside the cover 24 is capable of moving since the inlet port 26 and the outlet port 28 securely hold the drain tube 29. Thus, no tugging is sensed by the patient at the extremities of the drain tube 29 outside of the cover 24.

In a further embodiment, not illustrated, a reversible stepper motor pump may be used. The reversible stepper motor pump allows fluid to be metered precisely with an external load sensor. The reversible stepper motor pump preferably uses an in-line pressure sensor to insure a patient's safety.

Referring now to FIG. 4, the side elevational view of the portable pump apparatus 10 for CAPD of the present invention is shown. The rechargeable battery 15 supplies power to the pump 12 which is used to hasten the drainage process in the CAPD exchange. The present invention is capable of reducing drain times by approximately ten minutes, from a normal duration of fifteen minutes on the average, to about five minutes, depending on the patient position. The decreased drainage time provides an additional forty minutes of dwell time per day for improved clearances for the peritoneal dialysis patient. With the assistance of the present invention, therefore, the drainage can be completed in a significantly shorter time, making CAPD more convenient for the dialysis patient.

Another advantage of the present invention is that the drainage process is hastened regardless of the position of the patient. This advantage makes it possible for the patient to be walking, sitting or in any other ambulatory state. Because of the portable nature of the present invention, the belt clip 20 is provided for connecting the pump apparatus 10 to the patient's belt, waistband or the like. Again, this provides increased convenience for the user.

Further advantages of the present invention that provide for greater patient comfort and convenience are the following. Because of the portability of the pump apparatus 10, the patient may carry the pump apparatus 10 to work or use the pump apparatus 10 in a vehicle on the way to work. This portability provides great convenience to the user.

In a preferred embodiment, the pump apparatus 10 is very small, measuring approximately two inches high by three inches wide by two inches deep. The pump apparatus 10 is also lightweight. The pump apparatus 10 is ergonomically designed so that it is easy to load and operate by the patient. As mentioned above, the pump 12 is energized by a rechargeable battery 15 so that no external power source is required for connection to the pump 12, thus increasing portability.

In addition, the present invention provides several safety features. For example, when the peritoneum is nearly empty, or if occluded tubing is sensed, the pump apparatus 10 may automatically shut-off, and an alarm 46 may sound. Additional CAPD parameters capable of being sensed are possible. For example, temperature or conductivity can be sensed and can stop the reciprocating pump 12 until the correct condition of dialysate fluid is restored. Similarly, a pressure problem can also shut-off the pump 12.

FIG. 4 also illustrates the display 30 provided for the convenience of the user. The display 30 may be a digital, LCD-type display. Data relating to the drainage process can be shown on the display 30. For example, the volume of effluent displaced can be shown on the display 30. Thus, the display 30 is capable of providing information so that the patient knows when drainage is nearly complete. This is an important feature because the drainage flow rate decreases markedly when approximately 85% of the effluent is drained. It is unnecessary for the patient, therefore, to continue drainage for any great length of time beyond this point. Alternatively, an audible signal may be generated to warn the patient that drainage is nearly complete.

The conveniently displayed drainage volume information may also be used to monitor fluid clearance. In addition, urea clearance detection may also be incorporated into the present invention. The information may be displayed on the display 30 as well as stored in a memory 43 of a microprocessor 44 (see FIG. 4) for monitoring adequacy over time.

Of course, other parameters of interest to the CAPD patient can be displayed, and the present invention is not limited to the above-described parameters. Any parameter capable of being sensed and subsequently processed by a microprocessor, for example, may be displayed.

FIG. 5 illustrates a functional block diagram of an embodiment of the portable pump apparatus for CAPD of the present invention wherein like numerals represent like parts. As illustrated, the microprocessor 44 having the memory 43 for storing data and the like is provided. The microprocessor 44 is operatively connected to the motor 41. Also, the battery 15 and the speed control 18 are connected to each other and to the motor 41, which in turn drives the pump 12. The microprocessor 44 may also control the pump 12 and/or the motor 41.

Further, the microprocessor 44 is connected to the display 30 for providing the above-described parameters of interest to the CAPD patient. The memory 43 may also store the data.

In addition, the alarm 46 is connected to the microprocessor 44 for alerting the CAPD patient of any problems that may occur. Also, as explained above, urea clearance detection may be incorporated into the present invention. For example, a urea detector 50 is connected to the microprocessor 44 having the memory 43. Additional sensors, including for example, a volume sensor 52 for indicating a measure of displaced volume of fluid is connected to the microprocessor 44. In addition, a temperature sensor 54 and a pressure sensor 56 are connected to the microprocessor 44 to provide additional inputs for subsequent processing and display on the display 30. As indicated by a further block 58 shown in dashed lines, additional sensors may be provided to sense CAPD parameters that are subsequently processed by the microprocessor 44 so that they may be displayed on the display 30 for the patient's convenience and use. Certain parameters may also be displayed directly without further processing.

Although the present invention has been described primarily as a drainage device, it is intended to also assist in the fill process of CAPD. The pump apparatus 10 may also be used to hasten the fill process of the CAPD exchange. However, since the drain step takes about twice as long as the fill step, the device is especially advantageous for assisting the drainage.

It should be understood that various changes and modifications to the presently preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

We claim:

1. A portable pump apparatus for CAPD, the apparatus comprising:

a housing having a planar exterior wall partially defining an interior of the housing;

a pump located exterior to the planar exterior wall of the housing;

a power supply in the interior of the housing electrically connected to the pump to energize the pump;

a cover mounted to the planar exterior wall of the housing to enclose the pump, the cover having an inlet port and an outlet port defined by cut-out sections in the cover; and a tube extending substantially parallel to the planar exterior wall from a point exterior to the cover and in the inlet port, under the cover, and out the outlet port wherein the ports securely hold the tube restricting motion of the tube outside the cover.

2. The portable pump apparatus for CAPD of claim 1 further comprising:

a control means constructed and arranged for adjusting the speed of the pump.

3. The portable pump apparatus for CAPD of claim 1 further comprising:

a fastening means constructed and arranged on the housing for providing attachment to a patient.

4. The portable pump apparatus for CAPD of claim 1 wherein the power supply is a rechargeable battery.

5. The portable pump apparatus for CAPD of claim 1 wherein the pump is a reversible roller pump.

6. The portable pump apparatus for CAPD of claim 1 further comprising:

means for displaying CAPD information located on the housing.

7. The portable pump apparatus for CAPD of claim 1 further comprising:

means for processing operatively connected to the pump.

8. The portable pump apparatus for CAPD of claim 7 further comprising:

a volume sensor connected to the means for processing.

9. The portable pump apparatus for CAPD of claim 7 wherein the means for processing is a microprocessor.

10. The portable pump apparatus for CAPD of claim 7 further comprising:

means for storing CAPD data connected to the means for processing.

* * * * *